United States Patent
Schmid et al.

(10) Patent No.: US 9,931,278 B2
(45) Date of Patent: *Apr. 3, 2018

(54) DEVICE FOR DETECTING THE REMOVAL OF DRUGS

(71) Applicants: SEIBERSDORF LABOR GMBH, Seibersdorf (AT); AIT AUSTRIAN INSTITUTE OF TECHNOLOGY GMBH, Vienna (AT)

(72) Inventors: Gernot Schmid, Bromberg (AT); Manfred Bammer, Vienna (AT)

(73) Assignees: Seibersdorf Labor GmbH, Seibersdorf (AT); Austrian Institute of Technology GmbH, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 15/118,185

(22) PCT Filed: Feb. 2, 2015

(86) PCT No.: PCT/AT2015/050034
§ 371 (c)(1),
(2) Date: Aug. 11, 2016

(87) PCT Pub. No.: WO2015/120498
PCT Pub. Date: Aug. 20, 2015

(65) Prior Publication Data
US 2017/0165151 A1 Jun. 15, 2017

(30) Foreign Application Priority Data

Feb. 11, 2014 (AT) .............................. A 50103/2014
Mar. 10, 2014 (AT) .............................. A 50173/2014

(51) Int. Cl.
*A61J 7/02* (2006.01)
*H04W 4/00* (2009.01)
(Continued)

(52) U.S. Cl.
CPC .................. *A61J 7/02* (2013.01); *A61J 1/035* (2013.01); *G01N 27/025* (2013.01);
(Continued)

(58) Field of Classification Search
CPC .......... A61J 7/02; A61J 1/035; A61J 2200/30; G01N 27/025; H04B 5/0031; H04B 5/0081; H04W 4/008
See application file for complete search history.

(56) References Cited

U.S. PATENT DOCUMENTS 4,616,316 A * 10/1986 Hanpeter .............. A61J 7/0481
206/531
4,617,557 A * 10/1986 Gordon ..................... A61J 7/04
206/531
(Continued)

FOREIGN PATENT DOCUMENTS

DE 102012005443 A1 9/2013
WO 8909042 A1 10/1989

*Primary Examiner* — Jermele M Hollington
*Assistant Examiner* — Suresh K Rajaputra
(74) *Attorney, Agent, or Firm* — Laurence A. Greenberg; Werner H. Stemer; Ralph E. Locher

(57) ABSTRACT

A device detects the removal of drugs from a drug blister pack. The device contains a base for receiving the drug blister pack which has a base surface which is configured for contact with the electrically conducting, metal foil that closes the pockets. In the region of the pockets, the base has holes that are configured for the passage of the drugs present in the pocket. In the region of the holes one transmitting coil and at least two receiving coils are each arranged and extend around the respective hole. The receiving coils are associated with each other with respect to the transmitting coil and are arranged such that when the foil resting against the base in the region of the respective hole is undamaged the difference of the voltages induced in the receiving coils by an electric current in the transmitting coil lies below a predetermined threshold value.

12 Claims, 6 Drawing Sheets

(51) Int. Cl.
  *H04B 5/00* (2006.01)
  *A61J 1/03* (2006.01)
  *G01N 27/02* (2006.01)

(52) U.S. Cl.
  CPC ......... *H04B 5/0031* (2013.01); *H04B 5/0081* (2013.01); *H04W 4/008* (2013.01); *A61J 2200/30* (2013.01)

(56) References Cited

U.S. PATENT DOCUMENTS

| | | | | |
|---|---|---|---|---|
| 4,660,991 | A * | 4/1987 | Simon | A61J 7/04 116/308 |
| 5,072,430 | A * | 12/1991 | Eckernas | A61J 7/0481 206/534 |
| 5,836,474 | A * | 11/1998 | Wessberg | A61J 7/0481 221/2 |
| 6,973,371 | B1 * | 12/2005 | Benouali | A61J 1/035 221/15 |
| 8,091,790 | B2 * | 1/2012 | Mickle | B65D 75/327 235/435 |
| 8,120,492 | B2 * | 2/2012 | Scharfeld | G06K 19/07749 340/572.1 |
| 2003/0111477 | A1 * | 6/2003 | Niemiec | A61J 7/0481 221/2 |
| 2005/0241983 | A1 * | 11/2005 | Snyder | A61J 7/0481 206/539 |
| 2006/0144747 | A1 * | 7/2006 | Le | A61J 7/0481 206/531 |
| 2009/0283439 | A1 * | 11/2009 | Barndt | B65D 83/0463 206/531 |

* cited by examiner

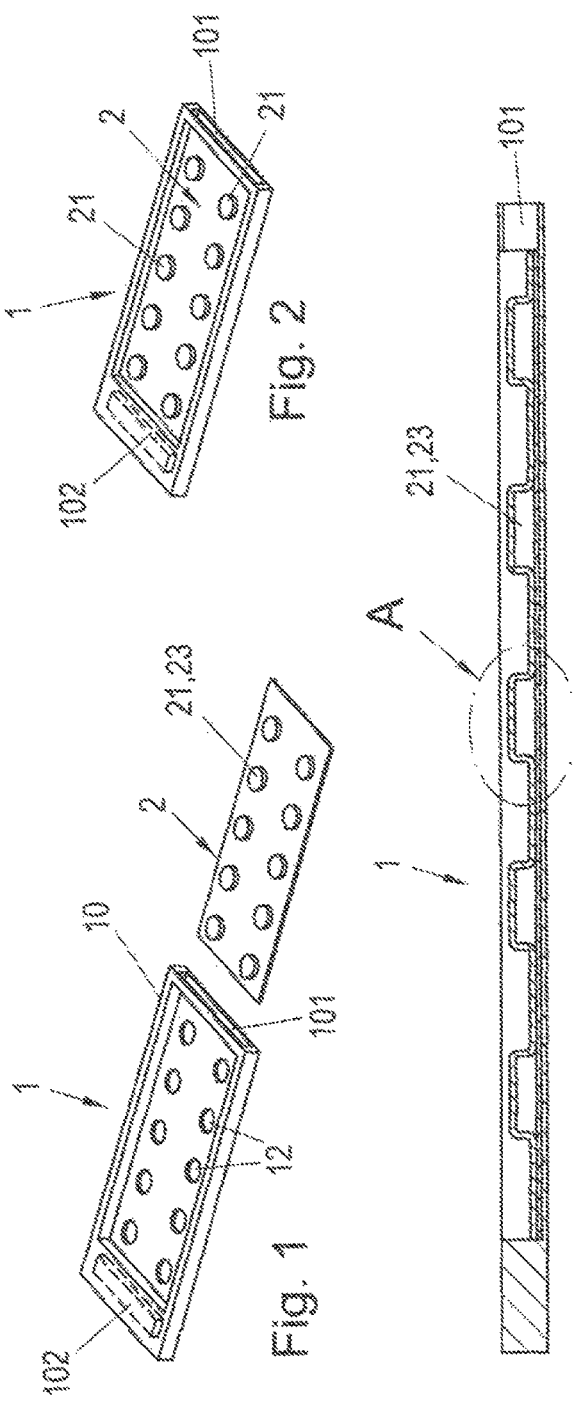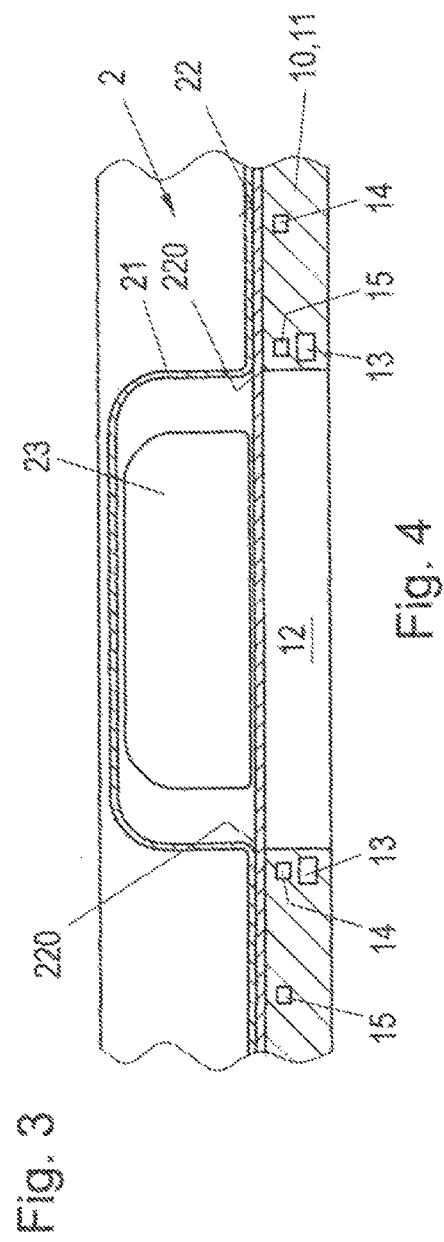

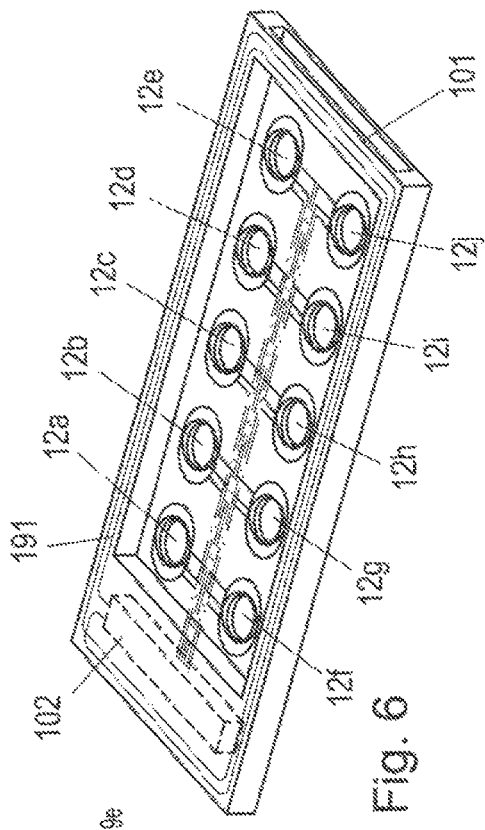
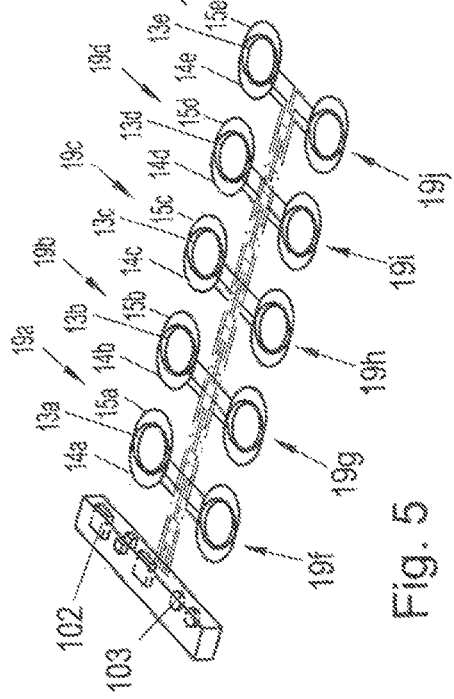
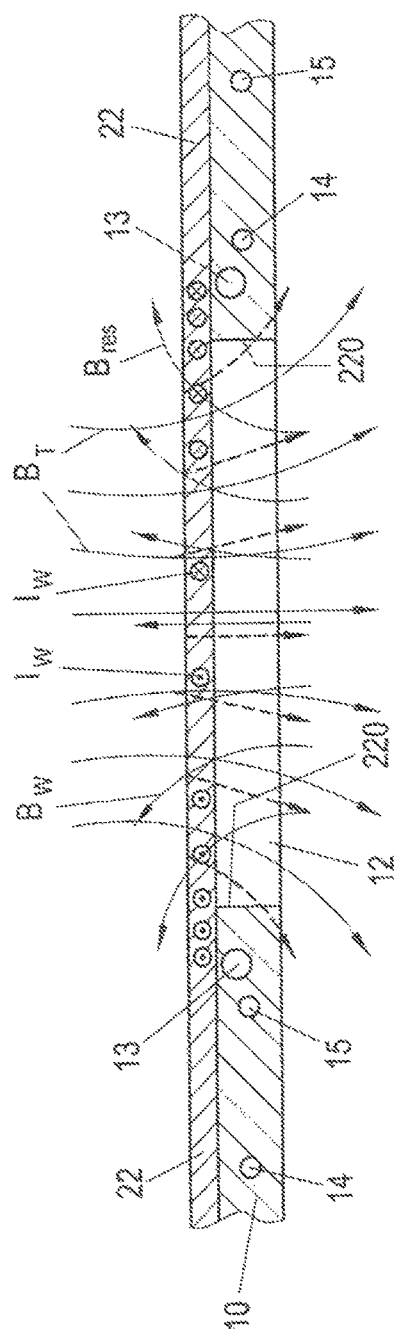

DEVICE FOR DETECTING THE REMOVAL OF DRUGS

BACKGROUND OF THE INVENTION

Field of the Invention

The invention relates to an apparatus for detecting the removal of medicaments from a drug blister pack.

The incorrect use of drugs constitutes a great problem in practice. In the case of a correct diagnosis and an ideal therapy plan, the success of the therapy can be drastically reduced if the patient does not use the drug correctly. In the case of some medicaments, e.g. anticoagulants, incorrect use can even have life-threatening consequences. The sources of error are multifaceted in practice: patients do not take medicaments or take the wrong medicaments; they take the correct medicaments in doses which are too small or too large. The World Health Organization WHO estimates that every second patient does not follow the instructions on the information leaflet or instructions by the medical practitioner. Experts assume that every fourth hospitalization and many deaths in Germany—more than 40,000 per annum with "cardiovascular" indications alone—can be traced back to incorrect use of medicaments. The reliable detection of correct and regular medicament uptake by the patients is therefore desirable, at least for certain classes of medicaments, firstly for health reasons and secondly for insurance purposes.

The currently existing solution approaches for detecting the tablet removal from press-through blister packs only have very restricted suitability for the mass market and have not yet prevailed because they are too complicated in terms of handling and manufacturing. These methods are based on the idea of destroying electrical conductor paths, antenna structures, components of resistor networks, etc. by pressing out the tablets, which is easily detectable by electronics connected to these structures. To this end, these structures, such as conductor paths, antennas, resistor networks, etc., must either be integrated directly into the sealing foil of the blister pack or subsequently applied onto the sealing foil, for example in the form of an adhesive foil, which contains the aforementioned structures with precise fit for each blister pack.

Therefore, relatively small clinical studies are currently based on the approach with foils which contain the aforementioned structures and are retrospectively adhered with precise fit onto the lower side of standard blister packs. As a result of the targeted provision of predetermined breaking points in the foil, the latter is pressed through or ripped open together with the blister pack sealing foil within the process of removing the tablet, and the structure element assigned to the respective blister pack pocket or tablet, e.g. a conductor path, antenna, etc., is destroyed or made inoperable. By way of electronics assigned to the structure elements, e.g. which are electrically connected to the foil by a contact strip, it is possible to record the time of the tablet removal and what tablet was removed.

The main problem of these solution approaches is the fact that the detection of the tablet removal is based on the destruction of the foil with the structure elements which was adhered onto the blister pack with precise fit. Therefore, a new foil with structure elements is required for each blister pack, leading to a linear increase of the costs with the number of required medicament blister packs. The alternative approach of already integrating the structure elements into the blister pack sealing foil is considered by the medicament producers as requiring too much outlay from a production point of view, being too complicated from a regulatory point of view and being unacceptable in view of the costs for the medicament packaging.

A solution with a reusable detection element for monitoring the tablet removable would therefore not only be paid back very quickly in large studies or within the scope of mass use during routine, but would also render obsolete the production of highly specialized blister packs.

Brief Summary of the Invention

It is therefore an object of the invention to simplify the detection of the tablet removal and to provide an apparatus which enables the detection even if the tablet producer has not provided such a possibility.

The invention solves this problem in the case of an apparatus of the type set forth at the outset by way of the features of patent claim 1.

In an apparatus for detecting the removal of medicaments from a drug blister pack, comprising a main body for accommodating the drug blister pack with a base area, which is embodied to rest against the electrically conductive, in particular metallic foil which seals off the pockets of the blister pack, provision is made for the main body to have holes in the region of the pockets of the blister pack, said holes being embodied for the passage of the medicaments situated in the pockets of the blister pack,
  wherein each hole is arranged in the region of one of the pockets in each case,
  wherein one transmission coil and at least two reception coils are arranged in the region of the holes in each case, said coils surrounding the respective hole, and
  wherein the reception coils are assigned to one another in respect of the transmission coil and arranged in such a way that, in the case where the foil resting on the main body in the region of the respective hole is undamaged, in particular free from rips, the difference of the voltages induced in the reception coils as a result of an electric current in the transmission coil lies below a predetermined threshold. A simple detection of the opening of a pocket of a drug blister pack, which can easily be carried out, is made possible as a result of this measure.

An advantageous implementation of an automated detection can be obtained by virtue of a detector unit which activates the transmission coil and measures the voltages across the reception coils and which establishes the difference between the voltages across the reception coils and, in the case where the difference of the two voltages exceeds a predetermined threshold, emits a message which indicates the presence of a rip in the metal foil sealing the respective pocket.

In order to have the removal information available for further processing, provision can be made of a recording unit, which activates the detector unit at predetermined intervals and establishes the presence of rips in the foils sealing off the pockets of the blister pack and stores information in this respect in a storage and keeps it available for further queries.

A simple data interchange is ensured by virtue of
  a short-range radio module, comprising an antenna and a communication controller, being connected to the detector unit and
  a storage, if a rip in the foil is identified, storing a message in this respect, in particular with the additional provision of a timestamp, wherein the detector unit is able to transfer information stored in the storage to an external data communications device.

An advantageous data interchange by way of RFID/NFC becomes possible if the short-range radio module is an RFID or NFC transponder, comprising a transponder antenna and a communication controller.

Here, for the simple and interference-free transfer to an external data communications device, provision is advantageously made for the transponder antenna to extend at least in part along the outer boundary of the main body of the apparatus.

Alternatively, the short-range radio module can also operate on the basis of a Bluetooth standard, wherein it has an antenna and a communication controller.

An advantageous evaluation of a pocket of a drug blister pack provides that provision is made for an excitation unit, which is connected to the transmission coil, and provision is made for two measuring units, which are connected to the reception coils, and the detector unit has a control unit, which actuates the excitation unit to excite the transmission coils and actuates the measuring units to measure the induction voltages across the reception coils, establishes the difference of the established induction voltages and outputs a signal in the case where the magnitude of the difference exceeds a predetermined threshold.

A simple evaluation of a multiplicity of pockets of a drug blister pack provides for a multiplexer for selecting a group, in each case comprising transmission and reception coils assigned to one another, to be connected to the detector unit, wherein the multiplexer has a common input for actuating the respective transmission antenna and two common outputs for obtaining the induction voltages obtained from the reception coils, wherein the common input is connected to the excitation unit and the common outputs are each connected to one of the measuring units, wherein the multiplexer has groups, each comprising two multiplex inputs and one multiplex output, which are addressable together and are each connected to the transmission and reception antennas, which are assigned to one another and arranged in the region of the same hole.

A particularly exact detection in the case of a simple design is achieved by virtue of the reception coils being arranged in symmetric fashion in respect of the holes and in respect of the transmission coil.

A simple design provides for the detector unit and the short-range radio module to be housed in a separate housing and the detector unit to be electrically connected by way of electric contacts, which are separable in a non-destructive manner, to the transmission antennas and reception antennas arranged at or in the main body.

What is furthermore particularly advantageous is an arrangement comprising an apparatus according to the invention and a drug blister pack with a number of pockets which are adjacent to the holes and in each case contain a medicament, and a foil sealing off the pockets, said foil being adjacent to the base area, wherein a group comprising a transmission coil and at least two reception coils in each case lies opposite each hole.

A preferred embodiment of the invention is illustrated in more detail on the basis of the following figures of the drawing.

BRIEF DESCRIPTION OF THE SEVERAL VIEWS OF THE DRAWING

FIG. 1 shows an embodiment of an apparatus for detecting the removal of medicaments and a drug blister pack.

FIG. 2 shows the apparatus depicted in FIG. 1, with the drug blister pack inserted into the apparatus.

FIG. 3 shows the combination depicted in FIG. 2, comprising the apparatus and the drug blister pack, in a cross section.

FIG. 4 shows a detail from FIG. 3.

FIG. 5 shows a circuit and an arrangement of transmission and reception coils.

FIG. 6 shows the transmission and reception coils depicted in FIG. 5 embedded in the apparatus for detecting the removal of medicaments.

FIG. 7 shows the field conditions in the region of a pocket of the medicament container in a sectional illustration.

DESCRIPTION OF THE INVENTION

Figure 8:
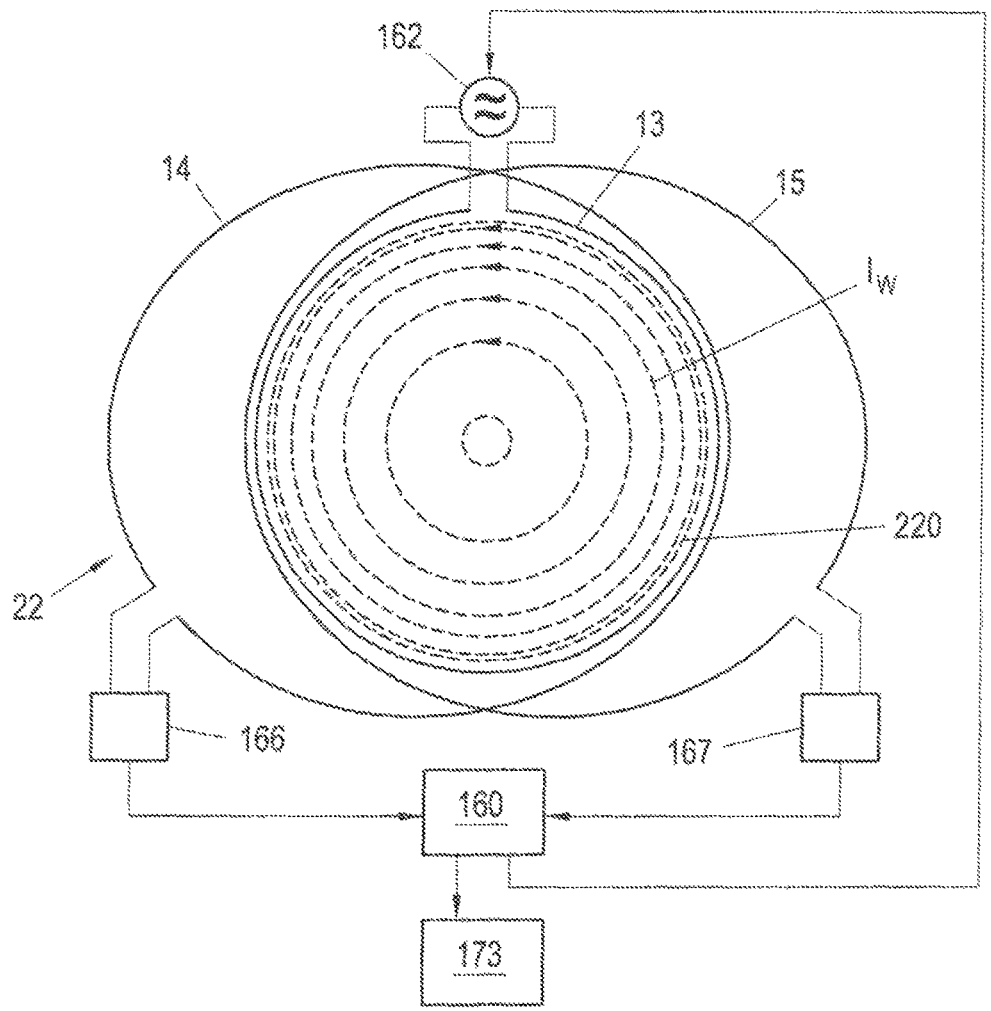
FIG. 8 shows, in detail, the field conditions in the region of an unopened and undamaged drug pocket, and the actuation and the readout of the transmission and reception coils.

FIG. 1 depicts a first embodiment of an apparatus according to the invention for detecting the removal of medicaments 23 from a drug blister pack 2. The apparatus 1 comprises a main body 10 with an opening 101 for inserting the drug blister pack 2 into the main body 10. At the position at which the pockets 21 of the blister pack 2 containing medicaments 23 are situated, the main body 10 of the apparatus 1 has a hole 12 in each case. Therefore, the pockets 21 lie directly opposite to the holes 12 such that the medicaments 23 situated in the pockets 21 of the blister pack 2 can be removed from the pockets 21, out of the blister pack 2 and out of the apparatus 1 through the holes 12.

FIG. 2 shows the drug blister pack 2 pushed through the opening 101.

FIG. 3 depicts the combination of the apparatus for detecting the removal of medicaments 23 and the drug blister pack 2 in a side view. FIG. 4 shows detail A from FIG. 3. Here, the region around the remaining pockets is embodied like in the region around the pocket 21 depicted in detail A. The pocket 21 constitutes a bulge in the drug blister pack 2, in which the medicament 23 to be removed, which is embodied as a tablet 23 in the present case, is situated. The pocket 21 is covered by an electrically conductive foil 22 in the planar continuation of the body of the drug blister pack 2, said foil sealing the pocket 21, wherein the foil 22 contains at least one planar continuous, electrically conductive layer or consists thereof. Three coils, namely a transmission coil 13 and two reception coils 14, 15, are situated in the region of the pocket.

FIG. 5 depicts the electronic and electrical components of the apparatus. Overall, FIG. 5 shows ten groups $19a \ldots 19j$ of transmission coils $13a \ldots 13j$ and reception coils $14a \ldots 14j$, $15a \ldots 15j$ assigned to one another. Each group $19a \ldots 19j$ determines the opening of in each case one of the pockets 21 of the blister pack 2. FIG. 5 also depicts an electronic circuit 102, which realizes a control unit 160 or detector unit 16 (FIG. 10), and a voltage supply 103.

FIG. 6 shows the apparatus with housing thereof, in which the transmission and reception coils 13, 14, 15, depicted in FIG. 5, are arranged, in particular cast or printed. Furthermore, FIG. 6 depicts an additional transmission antenna 191, by means of which the data established in the context of the medicament removal can be transferred to an external data communications device. In the present exemplary embodiment, the transmission antenna 191 extends along the outer boundary of the main body 10 of the apparatus 1.

In this configuration and in the case of an undamaged sealing foil 22, the eddy currents $I_W$ induced in the electrically conductive layer of the sealing foil on account of the magnetic field generated by the transmission antenna 13 are distributed in a circular manner in the region of the pocket 21, as depicted in FIG. 8. An induction voltage arises in each case in the two reception coils 14, 15 on account of the respective flux linkage, said induction voltages being established by the measuring devices 166, 167 and forwarded to a control unit 160.

FIG. 7 shows the field and current distribution in the case of an unopened pocket 21 and undamaged foil 22 in the region of the pocket. In a sectional view, FIG. 7 shows the arrangement of the transmission coil 13 and the two reception coils 14, 15, which surround the hole 12 of the main body 10 of the apparatus 1. Depicted above the hole 12 is the foil 22 which seals the pocket 21. On account of the excitation in the transmission coil 13, an undisturbed magnetic field $B_T$ would arise in the region of the hole 12 if the foil 22 were absent. However, a counter-acting field $B_W$ arises due to the eddy currents $I_W$ induced in the foil 22, said counter-acting field in superposition with the excitation field $B_T$ producing a resultant field $B_{res}$, which is substantially attenuated in relation to the original excitation field $B_T$.

If the foil 22 sealing the pocket 21 rips, the eddy currents induced in the foil 22 under the pocket 21 are distributed irregularly.

Figure 9:
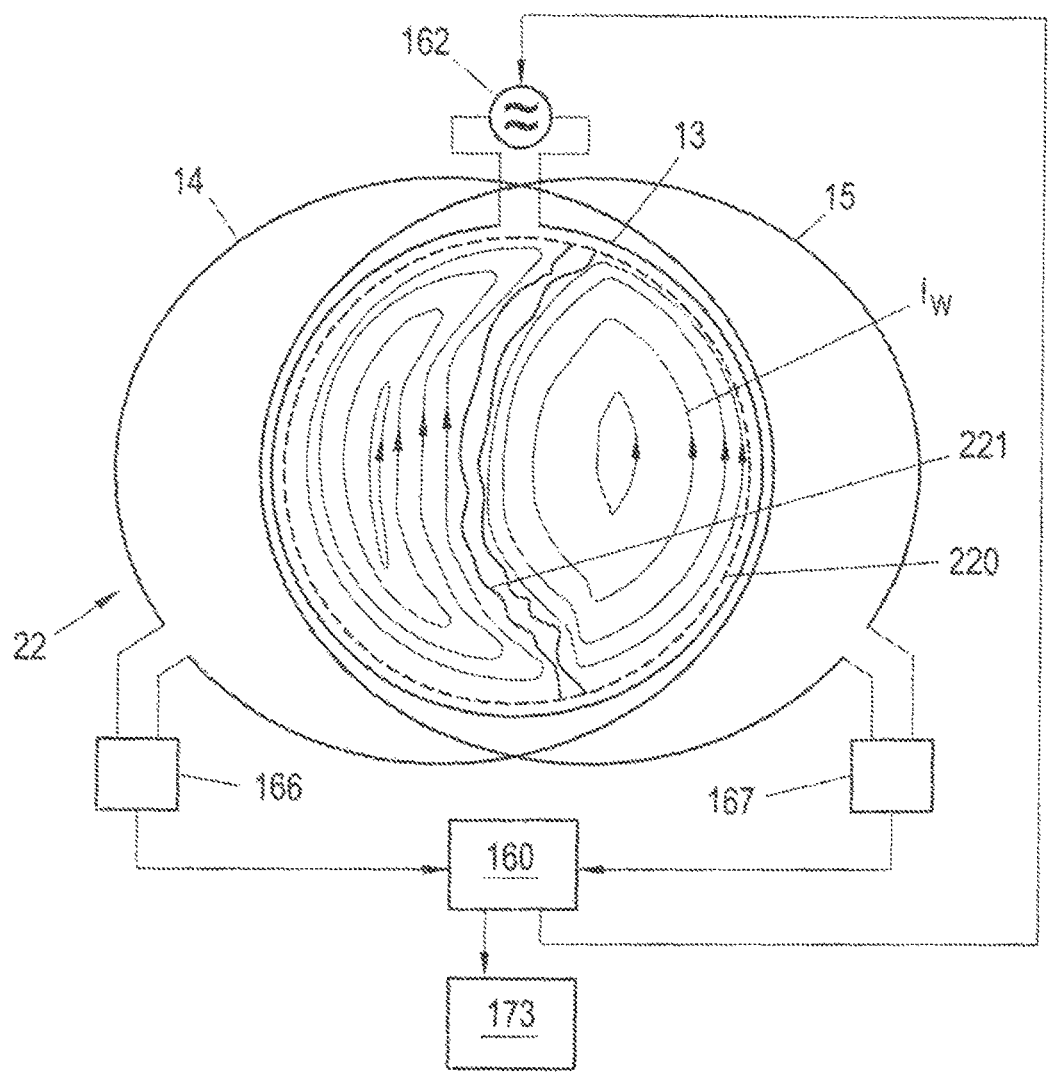
FIG. 9 shows, in detail, the field conditions in the region of an opened and ripped-open drug pocket and the actuation and the readout of the transmission and reception coils.

FIG. 9 depicts a current configuration of eddy currents $I_W$ when the foil 22 has ripped in the region of the pocket 21. Different voltages $V_A$, $V_B$ are induced in the two reception coils 14, 15 on account of the different alignment and size of the remains of the foil 22 which have arisen due to the rip, said different voltages being perceived via the voltage measuring devices 166, 167. In this case, the control unit 160 detects a voltage difference $\Box V$ and accordingly outputs a detection notification 173 indicating the detection of the ripping open or the removal of the medicament 23. Particularly large, and therefore easily detectable, voltage differences arise due to, in practice, the foil remains, which arise after the foil 22 was ripped open, at least slightly or partly turning out of the plane of the foil 22 underneath the pocket 21. As a result, the eddy currents induced in these foil remains also no longer flow in the plane of the foil 22, leading to a complex three-dimensional distribution of the resultant magnetic field $B_{res}$, which significantly deviates from the magnetic field distribution in the case of an undamaged sealing foil 22.

Figure 10:
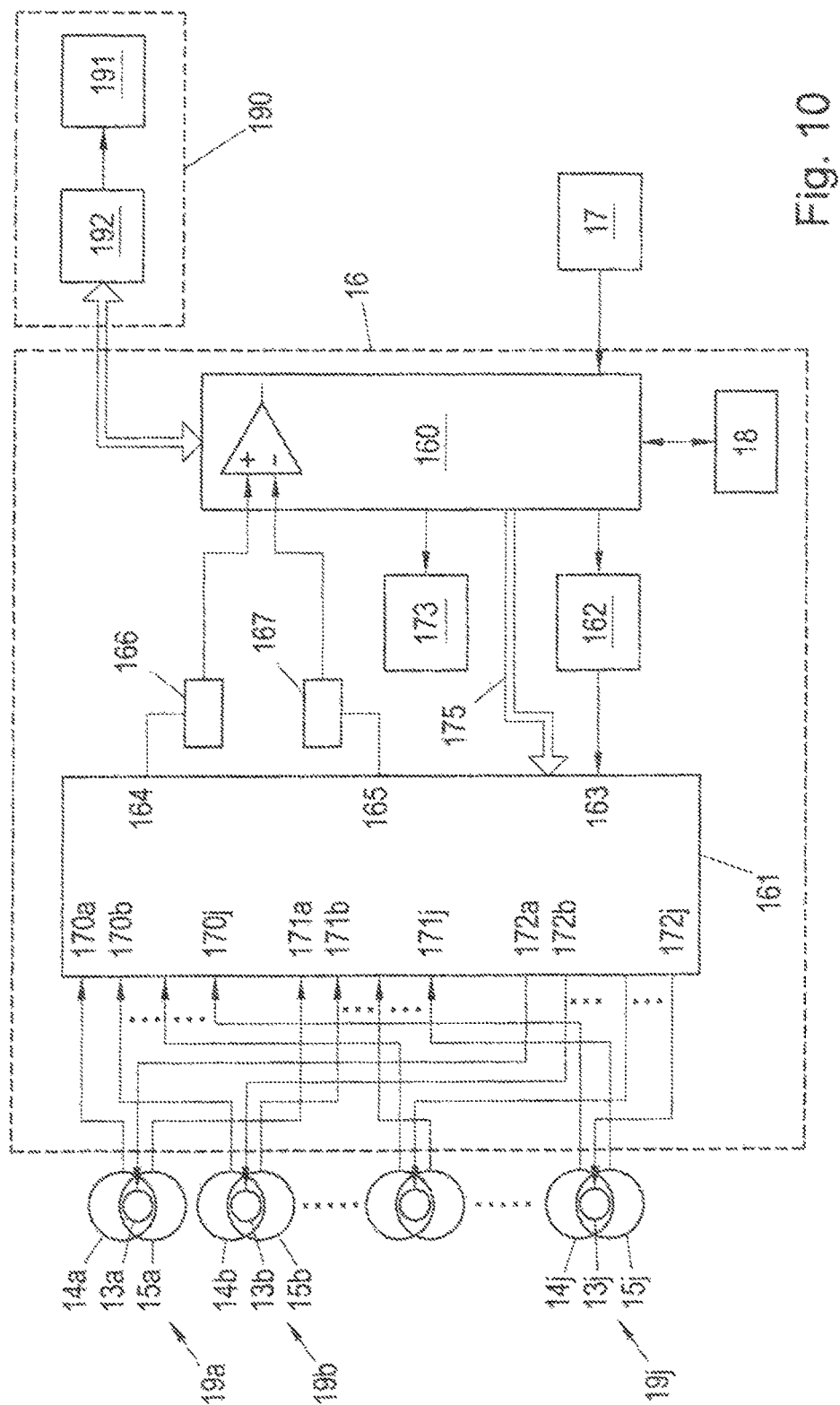
FIG. 10 schematically shows the electronic measurement or detection of the removal of medicaments.

FIG. 10 depicts a detector unit 16, by means of which the removal of a multiplicity of medicaments 23 can be detected from pockets in the same drug blister pack 2. Here, the detector unit 16 comprises the control unit 160 and a multiplexer 161 for selecting the respective group 19a . . . 19j, each comprising transmission and reception coils 13a . . . 13j, 14a . . . 14j and 15a . . . 15j assigned to one another. The multiplexer has a common input 163 for actuating the respective transmission antenna 13. The voltage generator 162, which is controlled by the control unit 160, is connected to this connector. Furthermore, the multiplexer 161 has two common outputs 164, 165, which are respectively assigned to one of the voltage measuring devices 166, 167. The results of the voltage measurement are transferred from the voltage measuring devices 166, 167 to the control unit 160. The control unit 160 furthermore sets by way of the multiplex control output 175 the respective group of transmission and reception coils 13a, 14a, 15a . . . 13j, 14j, 15j which are respectively addressed in order to establish whether the respective medicament 23 was removed from the respectively assigned pocket 21a . . . 21j. In a group-encompassing manner, the multiplexer 161 in each case has two multiplex inputs 170a, 171a . . . 170j, 171j and one multiplex output 172a . . . 172j, wherein each one of the groups is separately addressable in each case. The multiplex inputs and multiplex outputs, which are assigned to one another in groups 19a . . . 19j, are each connected to transmission and reception antennas 13a . . . 13j, 14a . . . 14j, 15a . . . 15j, which are assigned to one another and grouped and arranged in the region of the same hole 12.

In order to detect whether the metallic foil 22 resting against the main body 10 in the region of the respective hole 12 is undamaged, in particular free from rips, the difference of the voltage induced in the reception coils 14, 15 as a result of an electric current in the transmission coil 13 is measured. If it lies below a predetermined threshold, the foil 22 can be considered to be undamaged in the region of the respective hole 12.

The detector unit 16 measures the two voltages across the reception coils 14, 15 and determines the difference between the voltages across the reception coils 14, 15. In the case where the difference in the two voltages exceeds a predetermined threshold, said detector unit outputs a notification which indicates the presence of a rip in the metal foil 22 sealing the respective pocket 21.

In order to enable communication with an external data communications device, the control unit 160 is connected to a short-range radio module 190 comprising an antenna 191 and a communication controller 192. This short-range radio module can be an RFID or NFC transponder, as well as use an alternative wireless short-range communications technology, such as e.g. Bluetooth. Furthermore, the control unit 160 is connected to a storage 18, wherein the control unit 160, if the removal of a medicament 23 from one of the pockets is detected, in each case stores a message in this respect in the storage 18 and keeps it available for retrieval on the part of an external data communications device.

In particular, the detector unit 16 and the short-range radio module 190 can also be housed in a separate housing and the detector unit 16 is electrically connected to the transmission antennas 13 and reception antennas 14, 15 arranged on or in the main body 10 by way of non-destructively separable electric contacts.

Furthermore, FIG. 10 depicts a recording unit 17, which triggers the recording of the removal of medicaments at predetermined time intervals. The recorded values or messages which represent the removal of medicaments are stored in the storage 18.

Figure 11:
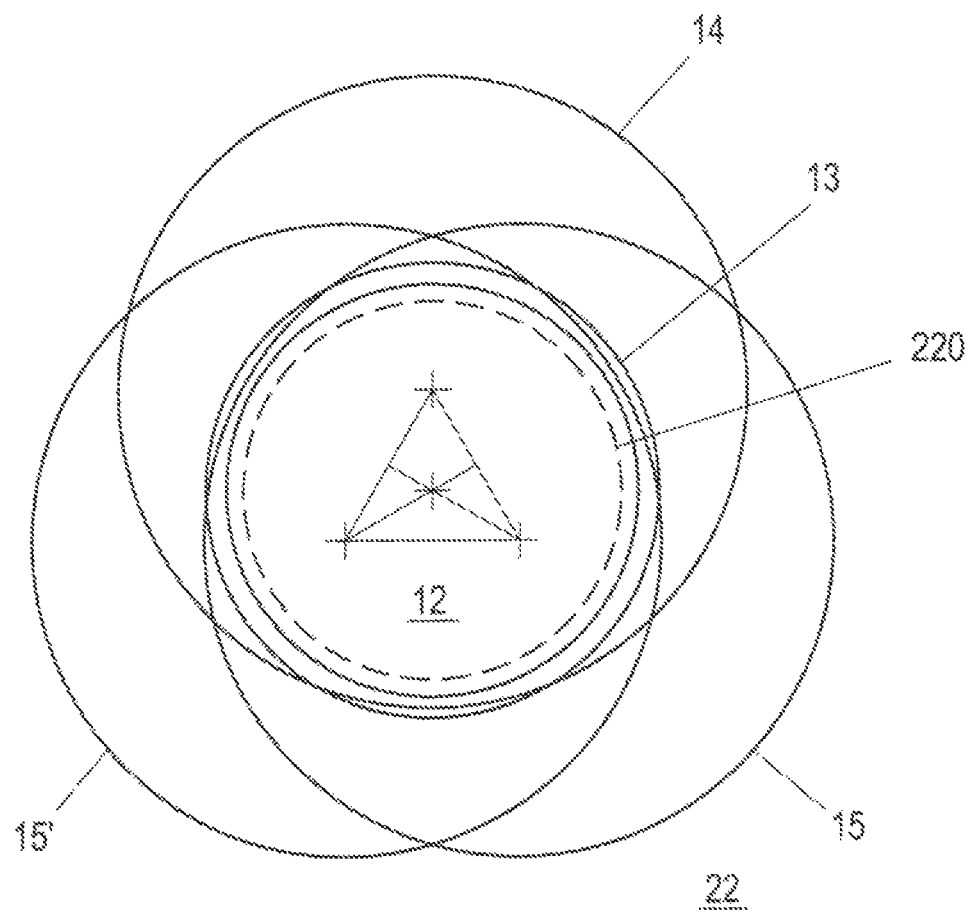
FIG. 11 shows an alternative coil arrangement with one transmission coil and three reception coils.

FIG. 11 depicts an alternative embodiment of the arrangement of transmission and reception coils. This special arrangement comprises a transmission coil 13 and three reception coils 14, 15, 15', which all have a circular embodiment. The centers of the reception coils 14, 15, 15' are situated on an equilateral triangle, the center of the transmission coil 13 lying at the centroid thereof. Furthermore, the edge 220 of the pocket 21 which is adjoined by the foil 22 has a concentric embodiment in respect of the transmission coil 13.

The invention claimed is:
1. An apparatus for detecting a removal of medicaments from a drug blister pack, the apparatus comprising:

a main body for accommodating the drug blister pack and having a base area embodied to rest against an electrically conductive foil sealing off pockets of the drug blister pack, said main body having holes formed therein in a region of the pockets of the drug blister pack, said holes being embodied for a passage of the medicaments situated in the pockets of the drug blister pack, each of said holes disposed in the region of one of the pockets in each case; and coils including one transmission coil and at least two reception coils disposed in a region of each of said holes in each case, said coils surrounding a respective hole, said reception coils are assigned to one another in respect of said transmission coil and disposed such that, in a case where the electrically conductive foil resting on said main body in the region of the respective hole is undamaged, a difference of voltages induced in said reception coils as a result of an electric current in said transmission coil lies below a predetermined threshold.

2. The apparatus according to claim 1, further comprising a detector unit which activates said transmission coil and measures the voltages across said reception coils and which establishes the difference between the voltages across said reception coils and, in a case where the difference of the two voltages exceeds the predetermined threshold, emits a message which indicates a presence of a rip in the electrically conductive foil sealing a respective pocket.

3. The apparatus according to claim 2, further comprising:
a memory; and
a recording unit which activates said detector unit at predetermined intervals and establishes a presence of rips in foils sealing off the pockets of the drug blister pack and stores information relating to the presence of the rips in said memory and keeps the information available for further queries.

4. The apparatus according to claim 2, further comprising:
a short-range radio module having an antenna and a communication controller, said short-range radio module is connected to said detector unit; and
a memory which, if a rip in the electrically conductive foil is identified, stores a message in this respect, with an additional provision of a timestamp, wherein said detector unit can transfer the information stored in said memory to an external data communications device.

5. The apparatus according to claim 4, wherein said short-range radio module is a radio frequency identification transponder or a near field communications transponder, containing said antenna and said communication controller.

6. The apparatus according to claim 5, wherein said antenna extends at least in part along an outer boundary of said main body of the apparatus.

7. The apparatus according to claim 4, wherein said short-range radio module having said antenna and said communication controller, operates on a basis of a Bluetooth standard.

8. The apparatus according to claim 2,
further comprising measuring units connected to said reception coils;
further comprising an excitation unit connected to said transmission coil; and
wherein said detector unit has a control unit which actuates said excitation unit to excite said transmission coils and actuates said measuring units to measure induction voltages across said reception coils, establishes a difference of established induction voltages and outputs a signal in a case where a magnitude difference exceeds the predetermined threshold.

9. The apparatus according to claim 8, further comprising a multiplexer for selecting a group, in each case containing said transmission coil and said reception coils assigned to one another, and is connected to said detector unit, wherein said multiplexer has a common input for actuating a respective said transmission antenna and two common outputs for obtaining the induction voltages obtained from said reception coils, wherein said common input is connected to said excitation unit and said common outputs are each connected to one of said measuring units, wherein said multiplexer has groups, each containing two multiplex inputs and one multiplex output, which are addressable together and are each connected to said transmission coil and said reception coils, which are assigned to one another and disposed in the region of a same said hole.

10. The apparatus according to claim 1, wherein said reception coils are disposed in a symmetric fashion in respect of said holes and in respect of said transmission coil.

11. The apparatus according to claim 4, wherein said detector unit and said short-range radio module are housed in separate housings and said detector unit is electrically connected by way of electric contacts, which are separable in a non-destructive manner, to said transmission coil and said reception antennas disposed at or in said main body.

12. A configuration, comprising:
a drug blister pack having a plurality of pockets holding medicaments and an electrically conductive foil sealing off said pockets; and
an apparatus for detecting a removal of said medicaments from said drug blister pack, said apparatus containing:
a main body for accommodating said drug blister pack and having a base area embodied to rest against said electrically conductive foil, said main body having holes formed therein in a region of said pockets, said holes being embodied for a passage of said medicaments situated in said pockets, each of said holes disposed in the region of one of said pockets in each case; and
groups of coils each including one transmission coil and at least two reception coils, one of said groups of coils disposed in a region of each of said holes in each case, said coils surrounding a respective hole, said reception coils are assigned to one another in respect of said transmission coil and disposed such that, in a case where sad electrically conductive foil resting on said main body in said region of said respective hole is undamaged, a difference of voltages induced in said reception coils as a result of an electric current in said transmission coil lies below a predetermined threshold.

* * * * *